United States Patent [19]

Ito

[11] Patent Number: 5,449,461
[45] Date of Patent: Sep. 12, 1995

[54] DISPLACEMENT COUNTERCURRENT CHROMATOGRAPHY

[75] Inventor: Yoichiro Ito, Bethesda, Md.

[73] Assignee: The United States of America as represented by the Department of Health and Human Services, Washington, D.C.

[21] Appl. No.: 263,924

[22] Filed: Jun. 21, 1994

[51] Int. Cl.⁶ .......................................... B01D 15/08
[52] U.S. Cl. ................................. 210/635; 210/657; 210/198.2
[58] Field of Search ............... 210/635, 656, 657, 658, 210/659, 96.1, 101, 198.2

[56] References Cited

U.S. PATENT DOCUMENTS

| | | | |
|---|---|---|---|
| 4,414,108 | 11/1983 | Ito | 210/198.2 |
| 4,430,216 | 2/1984 | Ito | 210/198.2 |
| 4,615,805 | 10/1986 | Ito | 210/657 |
| 4,849,110 | 7/1989 | Takata et al. | 210/656 |
| 5,114,589 | 5/1992 | Shibusawa et al. | 210/657 |
| 5,169,521 | 12/1992 | Oka et al. | 210/198.2 |
| 5,169,984 | 12/1992 | Cahnmann et al. | 562/447 |
| 5,215,664 | 6/1993 | Kitazume et al. | 210/635 |
| 5,217,608 | 6/1993 | Conway | 210/198.2 |
| 5,273,656 | 12/1993 | Anderson | 210/635 |
| 5,332,504 | 7/1994 | Ito et al. | 210/635 |
| 5,354,473 | 10/1994 | Ito | 210/635 |

OTHER PUBLICATIONS

Ito, Yoichiro, "Cross-Axis Synchronous Flow-Through Coil Planet Centrifuge Free of Rotary Seals for Preparative Countercurrent Chromatography. Part 1. Apparatus and Analysis of Acceleration," *Separation Science and Technology*, 22 (-10):1971-1987 (1987).

Ito, Yoichiro, "Cross-Axis Synchronous Flow-Through Coil Planet Centrifuge Free of Rotary Seals for Preparative Countercurrent Chromatography. II. Studies on Phase Distribution and Partition Efficiency in Coaxial Coils," *Separation Science and Technology*, 22(8-10):1989-2009 (1987).

Ito, Y., et al., "Cross-Axis Synchronous Flow-Through Coil Planet Centrifuge for Large-Scale Preparative Counter-Current Chromatography. I. Apparatus and Studies on Stationary Phase Retention in Short Coils," *J. of Chromatography*, 449:135-151 (1988).

Ito, Y., et al., "Cross-Axis Synchronous Flow-Through Coil Planet Centrifuge for Large-Scale Preparative Counter-Current Chromatography. II. Studies on Partition Efficiency in Short Coils and Preparative Separations with Multilayer Coils," *J. of Chromatography*, 449:153-164 (1988).

(List continued on next page.)

*Primary Examiner*—Ernest G. Therkorn
*Attorney, Agent, or Firm*—Townsend and Townsend Khourie and Crew

[57] ABSTRACT

The present invention provides a new method of pH-zone-refining countercurrent chromatography that can be operated in a manner analogous to displacement chromatography. The method uses a retainer base (acid) in the stationary phase to retain analytes in the column and a displacer acid (base) to elute the analytes in the decreasing (or increasing) order of $pK_a$ and hydrophobicity. The elution produces a train of highly concentrated rectangular solute peaks with minimum overlap. To use pH-zone refining CCC in a displacement mode, the mobile and stationary phases are switched. Thus, the original eluent becomes a retainer to retain analytes in the stationary phase, and the original retainer acid becomes a displacer to displace the analytes from the stationary phase to the mobile phase at the back of the solute bands.

The present method provides a distinct advantage over the pH-zone-refining countercurrent chromatography in the normal mode in that the eluted compound is provided as a salt-free acid or base in an organic solvent which can easily be evaporated. Additionally, the displacement mode of pH-zone-refining countercurrent chromatography is amenable to a ligand-affinity separation which may cover a broader range of analytes including nonionizable compounds. As with the normal mode, the present method can be used on a preparative scale.

19 Claims, 4 Drawing Sheets

OTHER PUBLICATIONS

Ito, Y., et al., "Cross-Axis Synchronous Flow-Through Coil Planet Centrifuge for Large-Scale Preparation Counter-Current Chromatography. III. Performance of Large-Bore Coils in Slow Planetary Motion," *J. of Chromatography*, 449:151-162, 1988.

Ito, Y., et al., "Improved high-speed counter-current chromatograph with three multilayer coils connected in series. IV. Evaluation of preparative capability with large multilayer coils," *J. of Chromatography*, 538:22-26 (1991).

Ito, Y., et al., "Cross-axis synchronous flow-through coil planet centrifuge (Type XLL) I. Design of the apparatus and studies on retention of stationary phase," *J. of Chromatography*, 538:59-66 (1991).

Ito, Yoichiro, "High-Speed Countercurrent Chromatography," *CRC Critical Reviews in Analytical Chemistry*, 17(1):65-143 (1986).

Ito, Yoichiro, "High-Speed Countercurrent Chromatography," *Nature*, 326(6111):419-420 (26 Mar. 1987).

Conway, Walter D., *Countercurrent Chromatography*, VCH Publishers, Inc., New York, pp. 1-115 (1990).

Cahnmann, H. J., et al., "Synthesis and characterization of N-bromoacetyl-3,3',5-triiodo-L-thyronine," *J. of Chromatography*, 538:165-175 (1991).

Weisz, A., et al., "Complementary use of counter-current chromatography and preparative reversed-phase high-performance liquid chromatography in the separation of a synthetic mixture of brominated tetrachlorofluoresceins," *J. of Chromatography*, 607:47-53 (1992).

DISPLACEMENT COUNTERCURRENT CHROMATOGRAPHY

This invention lies in the field of liquid-liquid partition chromatography, and in particular in the separation of acid or basic solutes from a mixture of such solutes using chromatographic techniques.

BACKGROUND OF THE INVENTION

Countercurrent chromatography (CCC) is a form of liquid-liquid partition chromatography which relies on the continuous contact between two immiscible solvents, one of which is mobile relative to the other, in a flow-through tubular column, free of any solid support matrix. The retention time of a solute in the phase contact region of the system is determined by the volume ratio of the solvents, the partition coefficient of the solute between the solvents, and the degree of contact between the solvents. Like other forms of liquid-liquid partition chromatography, one of the solvents serves as a carrier, drawing the solutes from the other solvent and carrying the solutes out of the column in the order of elution. This carrier solvent is thus referred to as the mobile phase, while the other solvent is referred to as the stationary phase, even though it is not strictly stationary in many applications of the method. Solvent mixing, retention of the stationary phase in the column, and solute partitioning all take place in the column by the aid of a suitable acceleration field established by gravity, centrifugal force or both, and the configuration of the column.

Most equipment used for CCC separations involves a coil of column tubing, a portion of which is filled with the stationary phase while the mobile phase is passed through it. By varying the length and diameter of the tubing, CCC has been used for both analytical and preparative separations.

The flow rate of the mobile phase may be varied by varying the field imposed on the column. Units which operate in the presence of a gravitational field only are restricted to slow flow rates, with the resulting separations typically requiring 1 to 3 days, to avoid displacing the stationary phase. A unit which operates in the presence of a centrifugal acceleration field of 40 g or more allows faster flow rates and permits separation times of only a few hours.

Separations by CCC may be performed using any immiscible pair of solvents, provided that the solvents differ in density to at least a slight degree. Both normal-phase and reverse-phase separations may be performed, with the more polar solvent as the stationary phase for normal-phase separations, and the less polar solvent as the stationary phase for reverse-phase separations.

The operational aspects of CCC are similar to the more conventional liquid-liquid chromatography (LLC). Typically, after the immiscible solvent phases are equilibrated relative to one another, the column is filled with the stationary phase. The sample is then injected into the column and elution with the mobile phase is begun. The centrifuge is then started and the eluting fractions are collected. Initially, the fractions are composed of the stationary phase which is displaced from the column. However, once hydrodynamic equilibrium between the phases is achieved, only small portions of the stationary phase will co-elute with the mobile phase. The collected fractions are monitored by any of a variety of means including spectroscopic methods and thin-layer chromatography.

Countercurrent chromatographic theory, as well as apparatus for performing the method, are described by Ito, Y., in "Principle and Instrumentation of Countercurrent Chromatography," in *Countercurrent Chromatography: Theory and Practice* Mandava, N. B., and Ito, Y., eds., pp. 79–442 (Marcel Dekker, New York, 1988) and by Conway, W. D., in *Countercurrent Chromatography: Apparatus, Theory and Applications* (VCH, New York, 1990). Most countercurrent chromatographs use a column which is formed into a helical coil. This coil is in turn mounted onto a column holder in various configurations relative to the means for rotating it and relative to the acceleration field that acts on it.

Each column and each type of rotation produce different types of mixing between the solvent phases and are particularly suited for specific separations. However, certain disadvantages to CCC exist.

One disadvantage associated with CCC is the increased peak width associated with increased retention time of the solute. This increased peak width makes detection of the solute more difficult, and requires a larger volume of eluate to be collected and processed in order to obtain a maximum yield of solute. This disadvantage is particularly acute when preparative separations are desired. Nevertheless, increased retention time is desirable in order to avoid coeluting impurities with the solute. Commonly-owned, U.S. Pat. No. 5,354,473, discloses a method for obtaining sharp elution peaks in analytical or semi-preparative CCC without decreasing the retention time of the solute, by adding a peak sharpening agent to either the stationary phase or the sample mixture. When acidic compounds are to be separated, the peak sharpening agent is an acid. When basic solutes are to be separated, the peak sharpening agent is a base.

More recently, an unusually efficient separation of mixtures of acids or bases has been described using a unique modification of the techniques of countercurrent chromatography. See, Ito, et al. U.S. Pat. No. 5,332,504, the disclosure of which is incorporated herein by reference. According to this modification, the two immiscible liquid solutions which are to serve as the stationary and mobile phases, respectively, are modified prior to the performance of the separation by rendering one of the phases acid and the other basic. Separation of a mixture of acids is then performed in a system in which the acidified solution serves as the stationary phase and the basified solution as the mobile phase. Conversely, separation of a mixture of bases is performed in a system in which the basified solution serves as the stationary phase and the acidified solution as the mobile phase. Individual acid or basic solutes separated by this method elute in contiguous, well-resolved, rectangularly shaped peaks, the solutes eluting in order of their partition coefficients (related to their $pK_a$ values and hydrophobicity) and the fractions within any single peak being of substantially constant concentration. In addition to differing partition coefficients, the combined fractions within each peak also differ in pH, successively increasing in the case of a basic mobile phase and successively decreasing in the case of an acidic mobile phase. For this reason, the technique has been referred to as "pH-zone-refining countercurrent chromatography."

Displacement countercurrent chromatography and pH-zone-refining countercurrent chromatography (in the normal mode) both entail certain advantages over previously known counter-current chromatography techniques. First, the method permits one to load the sample as a suspension into the separation column. Thus, mixtures of compounds that are only partially soluble in the solvent system can be separated efficiently. In addition, the lack or small degree of elution peak overlap permits one to separate mixtures of greater volume than before in any given column without loss of resolution. For example, columns which are otherwise recommended for separations of mixtures of a certain maximum size can be used for separating mixtures up to ten times that size or greater. Likewise, mixtures containing higher concentrations of the acid or basic solutes can be separated with no loss in resolution. As the concentration of solute increases, the separation simply produces a wider plateau for each solute.

SUMMARY OF THE INVENTION

It has now been discovered that a new method of pH-zone-refining countercurrent chromatography can be operated in a manner analogous to displacement chromatography. The method uses a retainer base (acid) in the stationary phase to retain analytes in the column and a displacer acid (base) to elute the analytes in the decreasing (or increasing) order of $pK_a$ and hydrophobicity. The elution produces a train of highly concentrated rectangular solute peaks with minimum overlap. To use pH-zone refining CCC in a displacement mode, the mobile and stationary phases are switched. Thus, the original eluent becomes a retainer to retain analytes in the stationary phase, and the original retainer acid becomes a displacer to displace the analytes from the stationary phase to the mobile phase at the back of the solute bands.

Capability of the method is demonstrated in the separation of dinitrophenyl amino acids in a two-phase solvent system composed of methyl tertiary-butyl ether and water. The present method provides a distinct advantage over the pH-zone-refining countercurrent chromatography in the normal mode in that the eluted compound is provided as a salt-free acid or base in an organic solvent which can easily be evaporated. Additionally, the displacement mode of pH-zone-refining countercurrent chromatography is more amenable for adapting to a ligand-affinity separation which may cover a broader range of analytes including nonionizable compounds. As with the normal mode, the present method can be used on a preparative scale.

Additional advantages and features of the invention and its preferred embodiments will be apparent from the description which follows.

BRIEF DESCRIPTION OF THE DRAWINGS

FIG. 4A shows the separation without spacer acids. FIG. 4B shows the separation with a spacer acid added to the sample solution and FIG. 4C shows the separation with a spacer acid added to the mobile phase.

DESCRIPTION OF THE PREFERRED EMBODIMENT

Figure 1A:
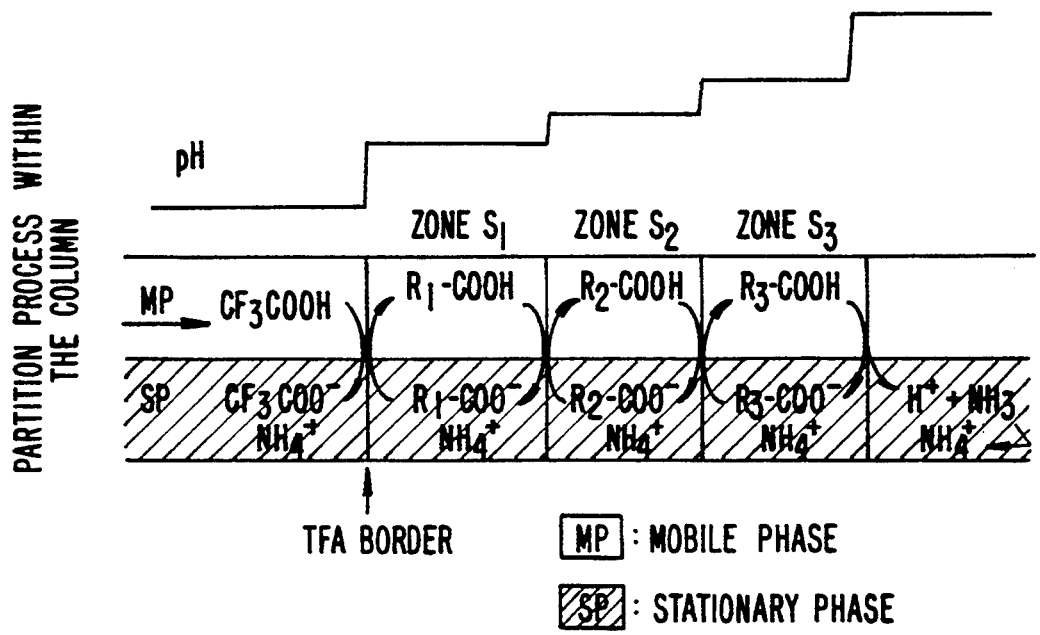
FIG. 1A schematically illustrates a portion of the separation column which contains the stationary aqueous phase in the lower half (shaded) and the mobile organic phase in the upper half. A sharp TFA border is indicated by a thick line across the column.

As used herein, the term "acidic compound" means an organic compound having an acidic functionality such as a carboxylic acid, phosphoric acid, phosphonic acid, phosphinic acid, sulfonic acid, sulfinic acid, phenol or the like.

As used herein, the term "basic compound" means an organic compound having a basic functionality such as an amine, imine, amidine, guanidine or the like.

As used herein, the term "separating" means to increase the amount of one component relative to the amounts of other components in a sample mixture. The mixture produced upon "separating" one component will be substantially free from the other components in the sample mixture, but may contain added quantities of solvents.

As used herein, the phrase "immiscible liquid phases" refers to liquids which may be partially miscible, but which separate into two phases having a liquid interface on standing. Typically, the two phases will comprise an organic phase and an aqueous phase. Suitable organic solvents include diethyl ether, hexane, ethyl acetate, methanol, methyl t-butyl ether, and acetonitrile.

As used herein, the term "identifying" means determining by spectroscopic means such as UV detection, refractive index detection, mass spectroscopy, and IR detection whether the desired compound is present in a particular sample or eluted fraction. Compounds may also be "identified" by a comparison of their elution times using HPLC.

The method of the present invention utilizes a countercurrent chromatographic centrifuge which may be any of the centrifuges generally used in other modes of countercurrent chromatography. A variety of these centrifuges have been described by Ito, Y., in "Principle and Instrumentation of Countercurrent Chromatography," in *Countercurrent Chromatography: Theory and Practice* Mandava, N. B., and Ito, Y., eds., pp. 79–442 (Marcel Dekker, New York, 1988) and by Conway, W. D., in *Countercurrent Chromatography: Apparatus, Theory and Applications* (VCH, New York, 1990).

Countercurrent chromatography utilizes the hydrodynamic behavior of two immiscible solvent phases mixing in a column to effect the separation of a solute from other components in a sample.

For the purposes of the following discussion and for distinguishing displacement countercurrent chromatography from pH-zone-refining countercurrent chromatography operating in the normal mode, reference should be made to the Table below.

TABLE

| Modes of pH-Zone-Refining Countercurrent Chromatography | | |
|---|---|---|
| | Displacement Mode | Normal Mode |
| To Separate Acidic Mixtures | | |
| Stationary Phase | Aqueous | Organic |
| Retainer | basic (NH3) | acidic (TFA) |
| Mobile Phase | Organic | Aqueous |
| Displacer | acidic (TFA) | basic (NH3) |

TABLE-continued

| Modes of pH-Zone-Refining Countercurrent Chromatography | | |
|---|---|---|
| | Displacement Mode | Normal Mode |
| To Separate Basic Mixtures | | |
| Stationary Phase | Aqueous | Organic |
| Retainer | acidic (HCl) | basic (Et$_3$N) |
| Mobile Phase | Organic | Aqueous |
| Displacer | basic (Et$_3$N) | acidic (HCl)* |

*In normal mode the displacer is more precisely referred to as the "eluant base (or acid)" as it does not enter the stationary phase to displace the analytes.

Any mixture of solvents which forms two phases on standing may be used. The phases may each be independently composed of organic solutions or aqueous solutions. In a preferred embodiment, one phase is composed of one or more organic solvents and the other phase is substantially aqueous. When chromatography is conducted with the aid of a centrifuge, preferred solvents are those which form two phases having a difference in density of at least 0.05 g/mL. The phases may be equilibrated relative to one another either prior to or during chromatography. Additionally, the phases may be equilibrated prior to the addition of a retainer or displacer to either phase. In a preferred embodiment, the phases are equilibrated in their neutral form by shaking them together and then allowing them to separate prior to charging the column with the stationary phase. When the phases are equilibrated in their neutral form, the stationary phase may be charged with a basic retainer (for separation of acidic solutes) or with an acidic retainer (for separation of basic solutes) prior to charging the chromatography column. Alternatively, the sample solution may be acidified with a retaining acid or basified with a retaining base.

The suitability of a desired two-phase solvent system can be determined by comparing the partition coefficient of the sample in both acidic environments, $K_a(U/L)$, and in basic environments, $K_b(U/L)$. To obtain a value for $K_a(U/L)$, the sample and retaining acid are added to a mixture of aliquots from the two phases (to give a concentration of approximately 10 mM). The phases are separated, diluted with an organic solvent such as methanol, and the absorbance of each phase is measured at an appropriate wavelength. The partition coefficient, $K_a(U/L)$, is obtained by dividing the absorbance of the upper phase by that of the lower phase. Similarly, to obtain a value for $K_b(U/L)$, the sample and a small amount of aqueous ammonia (28%) is added to a mixture of aliquots from the two phases. The mixture is equilibrated and the partition coefficient, $K_b(U/L)$ is measured as previously described. If $K_a(U/L) >> 1 >> K_b(U/L)$, the solvent system can be effectively used to separate an acidic sample. When $K_a(U/L)$ is 2 or less, the above test should be repeated with a less hydrophobic solvent system. When $K_b(U/L)$ is greater than 0.5, a less polar solvent system should be tested. The sample mixture may be prepared by partitioning the sample between amounts of the two phases prior to injection into the column or the sample may be injected without added solvents. Additionally, the sample need not be completely soluble in the two solvent phases but may be injected into the column as a suspension. In a preferred embodiment, the sample mixture is prepared by solubilizing the sample in small portions of each of the two solvent phases. In the case where the stationary phase is left neutral, the retaining acid or base is added to the sample mixture.

The motions which are applied to a CCC column are best described as corresponding to a solar system. In particular, a coiled column may undergo rotation about one or more axes. Solar coaxial motion is found when the coiled column is rotated about the axis of the coil. When the coil is mounted with its axis parallel and offset from a second axis, and the column is rotated only about the second axis, the rotation is termed solar satellite or solar eccentric motion. Planetary motion is provided when rotation occurs about two axes. When a coiled column is rotated about its own axis and also rotated about a second parallel axis, the motion is termed planetary coaxial motion. When a coiled column is rotated about a first external axis parallel to the axis of the coiled column, and the first external axis is simultaneously revolving about a second external parallel axis, the motion is termed planetary satellite or planetary eccentric motion.

In addition to configurations having parallel axes, there are also configurations in which the column axis is inclined or skewed relative to the external axes. Another type of planetary motion results when the two axes about which rotation occurs are orthogonal to one another. Methods utilizing this type of configuration are termed cross-axis CCC.

The columns employed in CCC are equally diverse. The majority are helical, but may vary in the material of fabrication, length, width, pitch of its winding, and mounting onto a column holder. Modern columns are typically constructed of polytetrafluoroethylene tubing which is capable of maintaining its shape and integrity while being exposed to a strong acceleration field. The inside diameter of the tubing is typically between 0.75 and 3 mm. While a single-layer coil may involve only a few meters of tubing, a multi-layer coil might contain more than 100 m of the tubing. Columns to be used for analytical purposes typically have an inside diameter which is more narrow and a length which is longer than a column used for preparative purposes. Additionally, helical columns may be either right-handed or left-handed. The handedness of the coils are determined by the direction in which the coils are wound onto a spool-shaped column holder. The helical column may be either a single layer or multilayer coil. For another column shape, the tubing may be wound onto a flexible core which is in turn coiled onto the column holder to produce a toroidal coil. Yet another type of column is a single layer spiral in which the tubing is wound in one layer onto a core and upon itself. The columns are further equipped with flow tubes which provide for the introduction of sample and mobile phases using an external pump. The tubes further allow the eluate to be collected using an automated fraction collector.

The present invention can be used with any of the columns and motions employed for CCC. The preferred apparatus is a high-speed countercurrent chromatographic centrifuge having a multilayer-coil separation column. The preferred motion is planetary motion (either coaxial or eccentric). Particularly preferred is synchronous planetary motion in which the number of revolutions about each of the two axes of rotation is the same within a particular period of time. The synchronous planetary motion provided by the centrifuge performs two functions. First, the synchronous rotation of the column holder constantly unwinds the twist of the flow tubes caused by revolution. This permits continuous elution through the rotating coil without the use of a conventional rotary seal device, which can be a potential source of leakage and contamination of collected fractions. Additionally, when the coiled column is coaxially mounted about the coil holder, the planetary motion of the holder unilaterally distributes two solvent phases in the column in such a way that one phase occupies the head side, and the other phase occupies the tail side of the coil. This head-tail relationship refers to the Archimedean screw force acting on the rotating coil, where all objects of different density are driven from the tail portion of the coil toward the head of the coil. This hydrodynamic phenomenon can be utilized for performing CCC in two ways. The coil can be entirely filled with a first liquid phase and eluted with the second liquid phase from the tail toward the head. Alternatively, the coil can be filled with the second liquid phase followed by elution with the first liquid phase from the head toward the tail. In either case the hydrodynamic phenomenon facilitates rapid movement of the mobile phase through the stationary phase, yielding extremely high retention of the stationary phase in the coil.

In one group of embodiments, the present inventive method is used to separate an acidic compound from other compounds in a sample mixture. Two immiscible solvent phases are equilibrated relative to one another to yield a two-phase mixture. A countercurrent chromatographic centrifuge column is then charged with a first liquid phase of the mixture. The first liquid phase is made basic by the addition of a retainer base, and the sample mixture containing the acidic compound to be separated is introduced into the column. The centrifuge is started and the second liquid phase, to which a displacer acid has been added, is passed through the column. Fractions containing the various components of the mixture are eluted, collected and identified.

The liquid phases are each independently an organic phase or an aqueous phase. In a preferred embodiment, the first liquid phase is an aqueous phase and the second liquid phase is an organic phase. In a further preferred embodiment, the first liquid phase is made basic by the addition of a retainer base. The retainer base should be inorganic so that it is retained permanently in the aqueous stationary phase. Suitable retainer bases include ammonia, dilute NaOH or dilute KOH. In a still further preferred embodiment, the first liquid phase is made basic with ammonia.

Figure 1B:
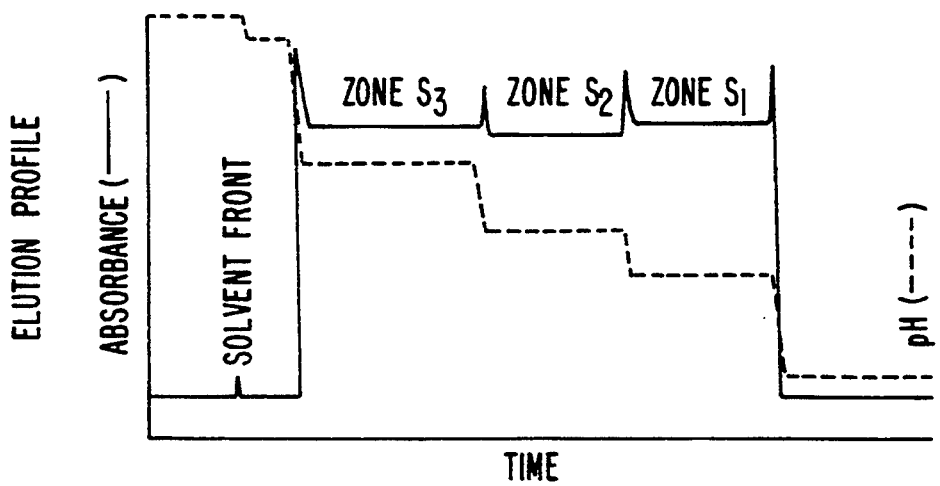
FIG. 1B schematically illustrates an elution profile for the separation of three carboxylic acids.

The mechanism by which separation occurs is best understood by referring to FIG. 1. A separation of analytes is initiated by filling the entire column with the stationary aqueous phase which contains a retainer, $NH_3$. This is followed by injection of a sample solution containing three major components (solutes $S_1$, $S_2$, and $S_3$). Then, the column is eluted with an organic mobile phase containing a displacer, TFA. As the mobile phase moves through the column by partially displacing the stationary phase, it distributes TFA to the stationary phase retained in the column according to the partition coefficient. This partition process depletes the TFA contents from the flowing mobile phase front resulting in formation of a sharp TFA front border across the column mainly due to the nonlinear isotherm of TFA. After the partition equilibrium is established, this sharp TFA border travels through the column at a uniform rate lower than that of the mobile phase front.

FIG. 1A schematically illustrates a portion of the separation column which contains the stationary aqueous phase in the lower half (shaded) and the mobile organic phase in the upper half. A sharp TFA border is indicated by a thick line across the column.

In the early stage of the separation, all solute molecules present on the right side of the TFA border are exposed to a high pH, mostly deprotonated to become a hydrophilic form ($R-COO^-$) and partitioned into the aqueous stationary phase. As the TFA front advances, these molecules are exposed to a low pH, protonated into a hydrophobic form ($R-COOH$) and transferred into the flowing organic phase. In other words, TFA in the mobile phase gradually displaces all solute molecules present in the stationary phase in a manner analogous to the action of the displacer in displacement chromatography.

As this process continues, the solute concentration at the front of the TFA border increases causing the pH to fall. In this situation, solute $S_1$ with the lowest $pK_a$ and hydrophobicity among the three components will act as a displacer on other two solutes to occupy the column space immediately after the sharp TFA border. It forms the first zone (zone $S_1$) by making a sharp front border. The competition continues among other two solutes in which solute $S_2$ with a lower $pK_a$ and hydrophobicity will form the second zone (zone $S_2$) which is in turn preceded by the third zone (zone $S_3$) consisting of solute $S_3$.

When this partition process is completed, a train of solute zones is formed in front of the TFA border as shown in FIG. 1A. As in displacement chromatography, each zone consists of a single species, is equipped with self-sharpening boundaries, and has the solute partition coefficient ($K_s$) (the solute concentration in the stationary phase divided by that of the mobile phase) equal to that of TFA ($K_{TFA}$) in the succeeding zone. As indicated earlier, All zones are arranged in a decreasing order of $pK_a$ and hydrophobicity and move together at the same rate determined by that of the succeeding TFA border.

As indicated by curved arrows, proton transfer and displacement of the solute molecule take place between the two neighboring species at each zone boundary. Ammonium created at the far front border (solute $S_3$) serves as counterions for all species. Charged impurities present in each solute zone are efficiently eliminated toward the zone boundaries of either side where they are accumulated to form narrow bands as seen in displacement chromatography. Consequently, the solutes are eluted in a successive rectangular peaks with minimum overlap and associated with sharp impurity peaks at their boundaries as shown in FIG. 2B. Each zone shows a distinct pH plateau in a downward staircase fashion as indicated by a dotted line.

In other preferred embodiments, the method of the present invention can be carried out on a preparative scale, using 0.01 to 100 g of the mixture which is to be separated. Additionally, the mixture to be chromatographed may be either a homogeneous solution or a suspension.

In another group of embodiments, the present inventive method is used for separating a quantity of a basic compound in a sample mixture. In these embodiments, two immiscible liquid phases are equilibrated relative to one another, then separated. A countercurrent chromatographic centrifuge column is charged with a first liquid phase to which a retainer acid is added either prior to or following its introduction into the column. The mixture containing a quantity of a basic compound to be separated is then introduced into the column. The centrifuge is started and the second liquid phase, to which a displacer base has been added, is passed through the column. Fractions containing the various components of the mixture are eluted, collected and identified.

As above, the liquid phases are each independently an organic phase or an aqueous phase. In a preferred embodiment, the first liquid phase is an aqueous phase and the second liquid phase is an organic phase. In a further preferred embodiment, the first liquid phase is made acidic by the addition of a retainer acid. As noted above for a retainer base, a retainer acid should be an inorganic acid which is retained in the aqueous stationary phase. Suitable retainer acids include dilute HCl, dilute sulfuric acid and dilute phosphoric acid. In a still further preferred embodiment, the first liquid phase is made acidic with HCl.

In another preferred embodiment, displacement countercurrent chromatography can be conducted on a preparative scale using 0.01 to 100 grams of the mixture containing the basic compound which is to be separated. In a still further preferred embodiment, the method can be used for separating a quantity of a basic compound in a suspension.

In yet another group of embodiments, the present inventive method is used for separating a quantity of a non-ionizable compound from other compounds in a mixture. In these embodiments, two immiscible liquid phases are equilibrated relative to one another, then separated. A countercurrent chromatographic centrifuge column is charged with a first liquid phase to which an affinity ligand is added either prior to or following its introduction into the column. The mixture containing a quantity of a non-ionizable compound to be separated is then introduced into the column. The centrifuge is started and the second liquid phase, to which a displacer has been added, is passed through the column. Fractions containing the various components of the mixture are eluted, collected and identified.

As above, the liquid phases are each independently an organic phase or an aqueous phase. In a preferred embodiment, the first liquid phase is an aqueous phase and the second liquid phase is an organic phase. In another preferred embodiment, the affinity ligand is a ligand which will complex with both isomers of an enantiomeric mixture and will complex more strongly (i.e. have a smaller dissociation constant) with the displacer.

In another preferred embodiment, displacement countercurrent chromatography can be conducted on a preparative scale using 0.01 to 100 grams of the mixture containing the non-ionizable compound which is to be separated. In a still further preferred embodiment, the method can be used for separating a quantity of a non-ionizable compound in a suspension.

The following examples are offered by way of illustration and are not meant to limit the scope of the invention.

EXAMPLES

Apparatus

A commercial model (Ito Multilayer Coil Separator/Extractor, Potomac, Md., USA) of the high-speed CCC centrifuge was used throughout the present studies. The detailed design of the apparatus is provided in U.S. Pat. No. 4,430,216. Briefly, the apparatus holds a multilayer coil separation column and a counterweight symmetrically at a distance of 10 cm from the central axis of the central axis of the centrifuge. The column holder is equipped with a plastic gear which is engaged to an identical stationary gear mounted around the central axis of the apparatus. This gear arrangement produces a desired planetary motion to the column holder, i.e., rotation and revolution of the holder in the same direction at the same rate. This planetary motion also prevents the flow tubes from twisting during revolution, thus permitting the elution of the mobile phase through the rotating column without the use of rotary seals which may cause leakage and contamination.

The separation column consists of a single piece of 1.6 mm ID, 160 m long PTFE (polytetrafluoroethylene) tubing (Zeus Industrial Products, Raritan, N.J., USA) wound around the column holder hub with 16 layers and 325 mL capacity. Both terminals of the column were connected to a flow tube (0.85 mm ID PTFE) (Zeus Industrial Products) by the aid of a set of tube connectors (Upchurch Scientific Co., Oak Harbor, Wash., USA) rigidly mounted on the holder flange.

The revolution speed of the apparatus was regulated with a speed controller (Bodine Electric Company, North Chicago, Ill., USA). An optimum speed of 600 rpm was used throughout the present studies.

A metering pump (Rainin Instruments Co., Emeryville, Calif., USA) was used to pump the mobile phase, a uv monitor (Uvicord S, LKB Instruments, Bromma/Stockholm, Sweden) for measuring the absorbance of the effluent at 206 nm and a fraction collector (Ultrorac, LKB Instruments) to collect fractions. In order to prevent formation of negative pressure which may result in sucking an extra volume of the mobile phase through the check-valves of the metering pump, a narrow-bore PTFE tubing (0.3 mm ID×5 m) (Zeus Industrial Products) was placed at the outlet of the monitor to restrict the flow.

Reagents

Methyl tertiary-butyl ether, methanal, and trifluoroacetic acid (TFA) were glass-distilled chromatographic grade (Burdick and Jackson Laboratories, Muskegon, Mich., USA). Ammonium hydroxide, hydrochloric acid, acetic acid, propionic acid and n-butyric acid were of reagent grade (Fisher Scientific Company, Fair Lawn, N.J., USA). Dinitrophenyl (DNP) amino acids used in the present studies include N-2,4-DNP-L-aspartic acid (DNP-asp), N-2,4-DNP-DL-glutamic acid (DNP-glu), N,N'-2,4-diDNP-L-cystine (diDNP-$(cys)_2$), N-2,4-DNP-L-alanine (DNP-ala), N-2,4-DNP-L-proline (DNP-pro), N-2,4-DNP-L-valine (DNP-val) and N-2,4-DNP-L-leucine (DNP-leu) (Sigma Chemical Co., St. Louis, Mo., USA).

Preparation of Solvent Phases and Sample Solutions

A pair of solvent phases used in the present studies was prepared as follows: A solvent mixture composed of methyl tertiary-butyl ether and distilled water in an arbitrary volume ratio was thoroughly equilibrated in a separatory funnel at room temperature and the two phases were separated. The upper organic phase was acidified with TFA (displacer) and used as the mobile phase. When desired, spacer acids such as propionic acid and n-butyric acid were added to the stationary phase. To the lower aqueous phase, $NH_3$ (retainer) was added and it was used as the stationary phase. In the basic studies, the effects of the eluent acid and retainer base were investigated by varying the concentration of these key reagents.

The sample solutions were prepared by dissolving the sample mixture in the stationary upper phase and a small amount of methyl tertiary-butyl ether was added to form two phases. In some experiments, spacer acids were added to the sample solution. The sample volume ranged from 5 mL to 40 mL according to the sample size. The sample mixture was only partially soluble in the above sample solution and was sonicated for several minutes to disperse undissolved particles before injection into the column.

Separation Procedure

In each separation, the column was first entirely filled with the aqueous stationary phase and the sample solution was injected through the sample port. Then the organic mobile phase was eluted through the column at a flow rate of 3.3 mL/min in the tail to head elution mode while the apparatus was rotated at 600 rpm. The effluent from the outlet of the column was continuously monitored by the absorbance at 206 nm through a uv monitor and collected into test tubes (3.3 mL/tube or 1 min/tube) with a fraction collector. After the desired peaks were eluted, the apparatus was stopped, and the column contents were collected into a graduated cylinder by connecting the inlet of the column to a $N_2$ line pressured at 80 psi. Then, the percentage retention of the stationary phase relative to the total column capacity was computed from the volume of the stationary phase collected from the column.

Analysis of Fractions

The pH value of each fraction was manually determined with a portable pH meter (Accumet Portable Laboratory, Fisher Scientific Company, Pittsburgh, Pa., USA).

DNP amino acids were identified by their partition coefficient values in a standard two-phase system composed of chloroform/acetic acid/0.1M HCl (2:2:1). An aliquot of each fraction (usually 1 mL) was delivered into a test tube and dried under vacuum (Speed Vac Concentrator, Savant Instruments, Inc., Hicksville, N.J., USA). Then, 2 mL of the standard solvent system, 1 mL each phase, were added to each tube and the contents were vigorously shaken to equilibrate the solute between the two phases at room temperature. After clear two layers were formed, an aliquot of each phase (usually 100–200 μL) was diluted with 2 mL of methanol and the absorbance was determined at 430 nm with a Zeiss PM6 spectrophotometer.

Example 1

This example describes the separation of a mixture of seven N-(2,4-dinitrophenyl)amino acids using displacement countercurrent chromatography according to the method described above.

Seven DNP amino acids, each 100 mg, were eluted as a broad rectangular peak. The partition coefficient studies on each fraction, however, revealed that it consisted of a series of narrow rectangular peaks of individual components with minimum overlap. These peaks are arrange according to the $pK_a$ and hydrophobicity of the components: DNP-leucine which has the highest $pK_a$ and hydrophobicity eluted first followed by other components in a decreasing order of $pK_a$ and hydrophobicity. As noted above, each component formed a pH plateau in a downward staircase fashion. Some irregularity of the pH level at the diDNP-cystine peak may be due to its significantly lower pH in the organic mobile phase than that in the aqueous mobile phase.

Example 2

This example illustrates the effect of displacer (TFA) concentration and the effect of retainer ($NH_3$) on the separation of three acidic components.

In the first series of studies, the concentrations of the displacer (TFA) in the organic mobile phase were varied from 0.02% (2.6 mM) to 0.16% (20.5 mM) while the concentration of the retainer ($NH_3$) in the aqueous stationary phase was fixed at the 0.1% (11 mM). In the second series of studies, the concentration of the retainer ($NH_3$) in the stationary phase was varied from 5.5–44 mM while that of the displacer (TFA) was fixed at 0.4% (10.8 mM) in the mobile phase.

In each separation, the column was first filled with the aqueous stationary phase followed by injection of a sample mixture consisting of 100 mg each component in 5 mL solvent (4 mL lower phase and 1 mL methyl t-butyl ether). Then, the column was rotated and eluted with an acidified organic phase at a flow rate of 3.3 mL/min. The effluent from the outlet of the column was continuously monitored with a uv monitor at 206 nm and collected in test tubes at one minute intervals (3.3 mL/tube). From the resulted chromatogram, the average solute concentration was estimated from the width of each peak. The partition coefficient of the displacer TFA (which is equal to that of each DNP amino acid) was also computed from the retention volume of the sharp front border of TFA together with the retention of the stationary phase and the total column capacity.

Figure 3A:
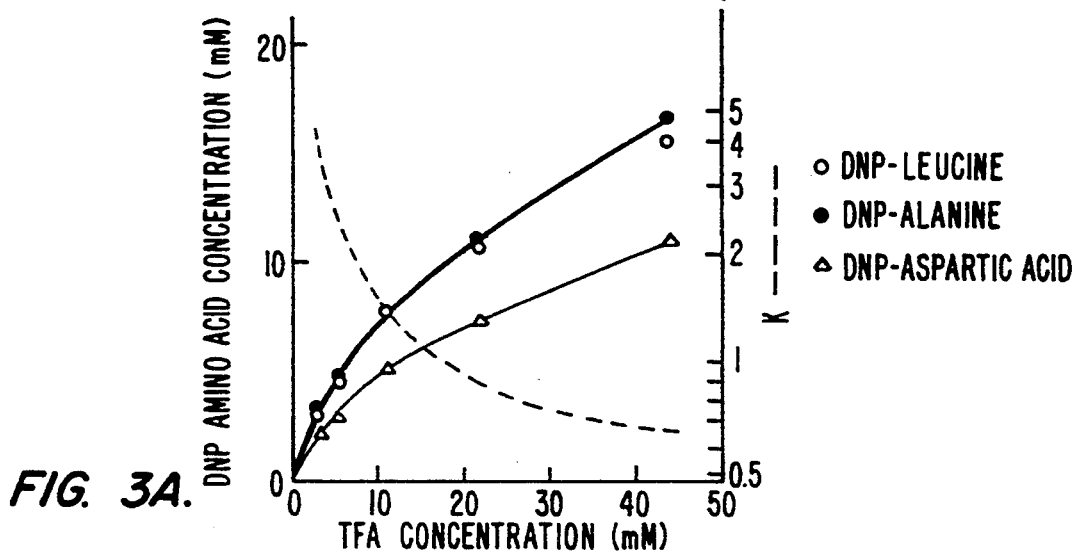
FIG. 3 shows the effect of TFA concentration (FIG. 3A) and NH3 concentration (FIG. 3B) on the recoveries of three DNP-amino acids.
Figure 3B:
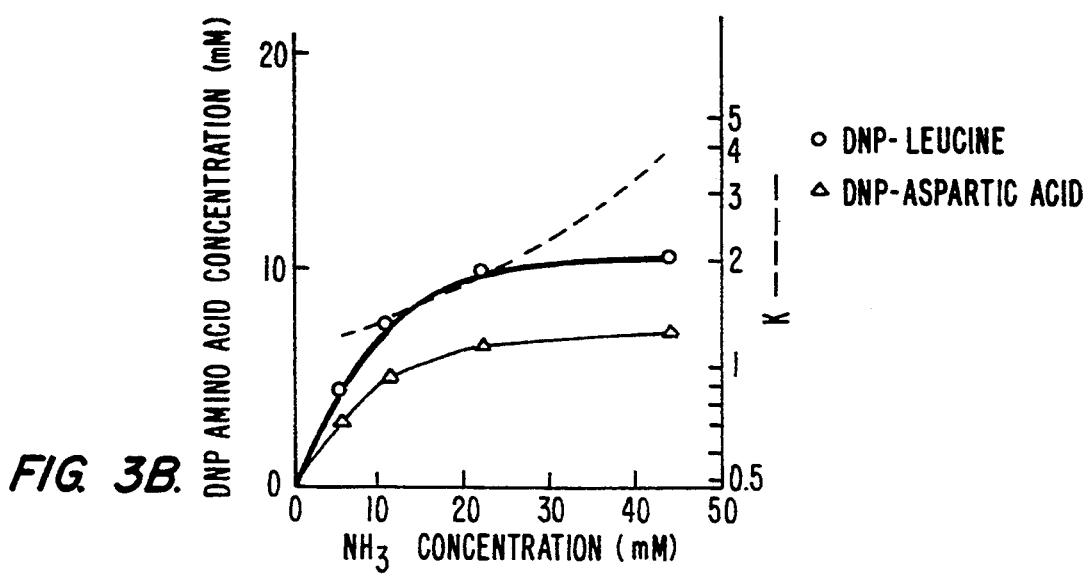

The results are shown in FIG. 3 where the solute concentrations (open circles for DNP-leu, solid circles for DNP-ala and triangles for DNP-asp) are plotted against the concentrations of the displacer TFA in the mobile phase (FIG. 3A) and the retainer $NH_3$ in the stationary phase (FIG. 3B). In both cases, the solute concentrations increase with an increased concentration of either TFA or $NH_3$ but more affectively with that of the former. In both diagrams the concentrations of monovalent acids (DNP-leu and DNP-ala) are approximated by $C_{NH_3}/K_{TFA}$ (original $NH_3$ concentration in the stationary phase divided by the partition coefficient of TFA) as shown by thick solid lines, indicating that the solute concentration in the stationary aqueous phase is close to that of the ammonium counterion. However, the plots of the divalent acid (DNP-asp) fall at about ⅔ of the above value shown by thin solid lines. Similar results were obtained in other divalent amino acids such as DNP-glutamic acid and diDNP-cystine.

On the other hand, the partition coefficient values of TFA (K) show completely opposite trends between these two diagrams. The K value (dotted line) decreases as the TFA concentration in the mobile phase increases (FIG. 3A) but it increases as the $NH_3$ concentration in the stationary phase increases (FIG. 3B). However, under all the applied experimental conditions, three DNP amino acids were well resolved and eluted as fused rectangular peaks with minimum overlap.

Example 3

This example illustrates the separation of three DNP-amino acids using spacers either in the sample solution or in the mobile phase.

Two spacer organic acids, propionic acid and n-butyric acid, were selected for separating DNP-leucine, DNP-alanine and DNP-aspartic acid. Selection of the spacer acids was based on the results of preliminary experiments where various organic acids and DNP amino acids were cochromatographed to investigate the order of their elution.

Figure 2:
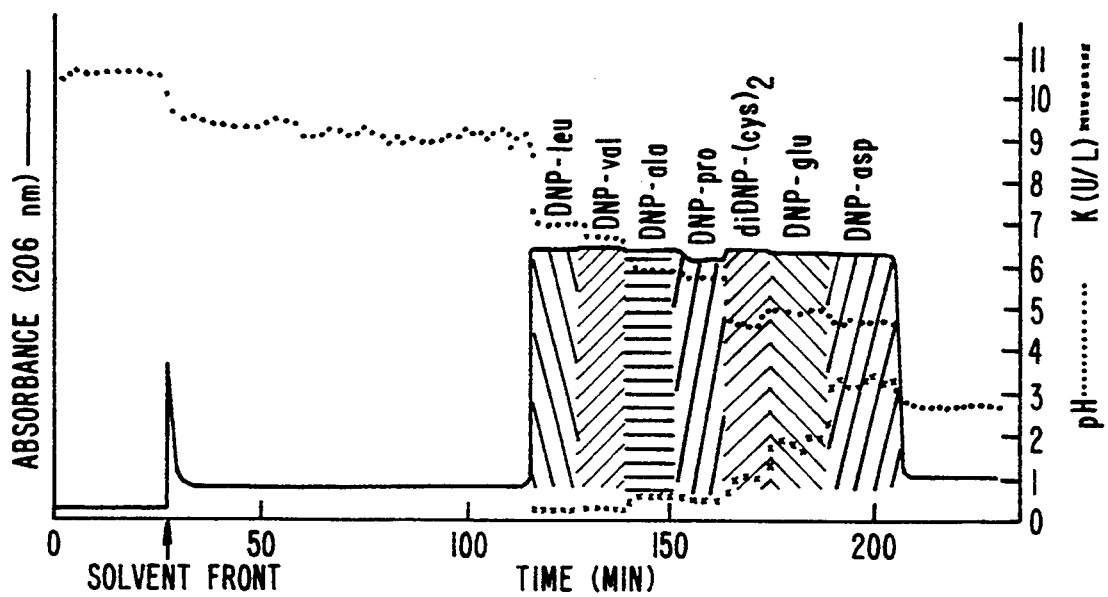
FIG. 2 shows the separations of seven amino acids as described in Example 1.
Figure 4A:
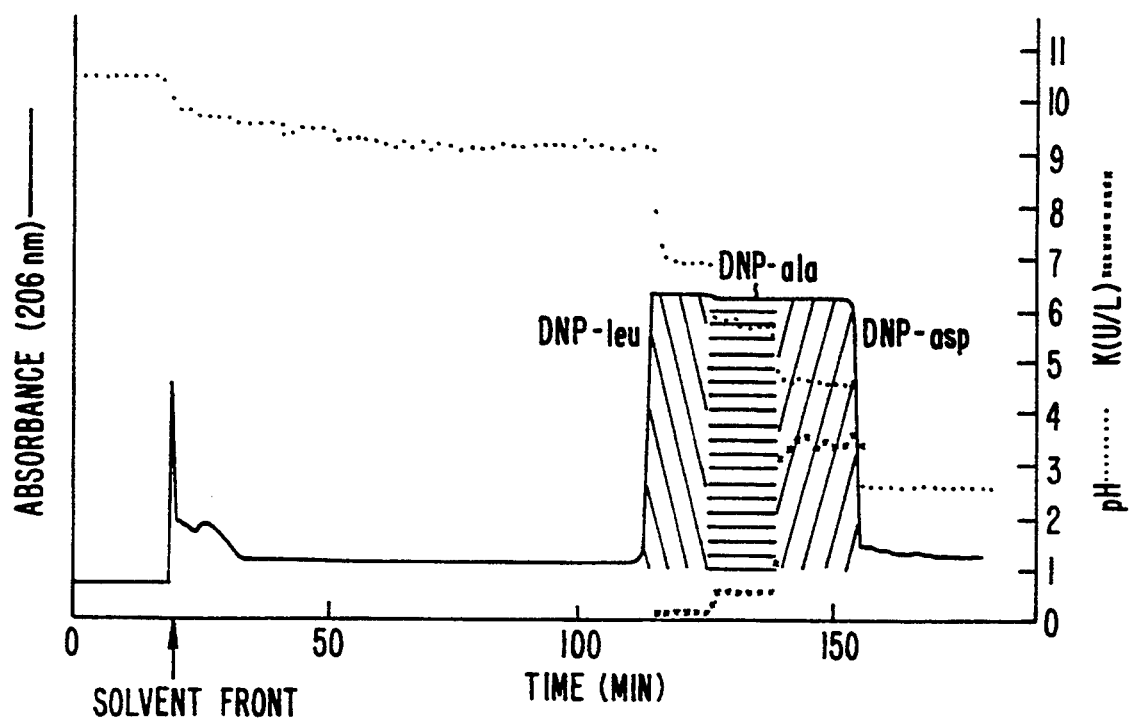
FIGS. 4A–4C illustrate the effect of added spacer acids to the separation of three DNP-amino acids.
Figure 4B:
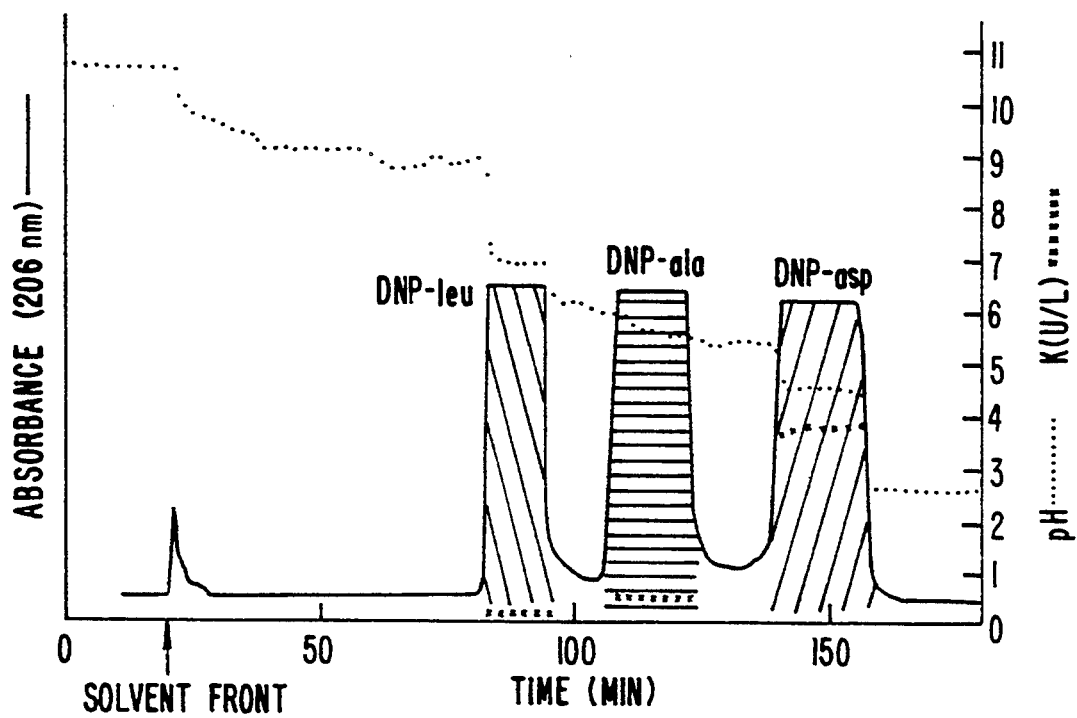
Figure 4C:
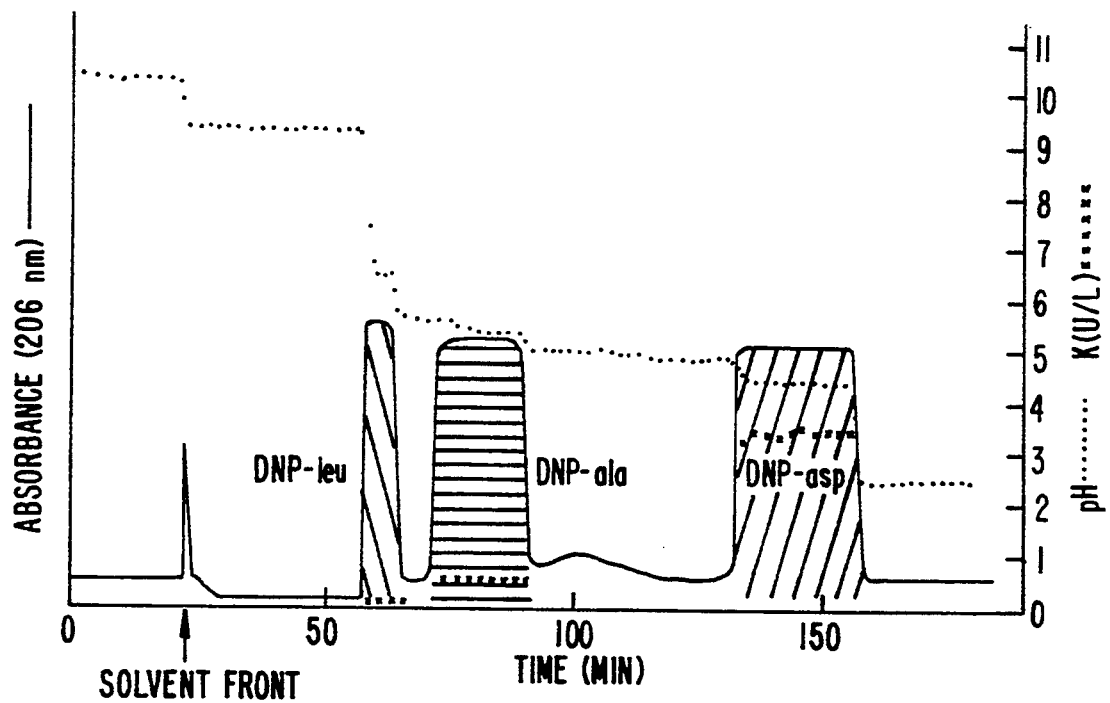

FIGS. 4A–C show separations of the three DNP amino acids without spacer acids (FIG. 4A), with the spacer acids in the sample solution (FIG. 4B) and with the spacer acids in the mobile phase (FIG. 4C). In FIG. 4A, three components were eluted as a single rectangular peak as shown in FIG. 2. When the spacer acids (each 50 µL) were introduced into the sample solution, DNP amino acids were completely resolved into three rectangular peaks each corresponding to the single species as labeled in the chromatogram (FIG. 4B). In this case, the two spacers show similar widths and the original peak width for each component is preserved. When the same spacer acids were introduced into the mobile phase (each 0.08%), however, the width and the retention time of each peak was altered in such a way that the first peak became narrower and eluted much earlier while the third peak became much broader compared with those in FIG. 4A. The peak spacing also became different: the width between the first and the second peaks is much narrower than that between the second and the third peaks. These changes were mainly produced by a steady supply of the spacer acids through the mobile phase which increased the traveling rate of the front border of each spacer acid and the preceding solute band.

The above results indicate that for uniform spacing and preservation of the original peak width of each component the spacers should be introduced locally in the sample solution rather than in the mobile phase.

Example 4

This example illustrates the separation of a mixture of three DNP amino acids. The mixture contains 0.5 g each of the amino acids.

Figure 5:
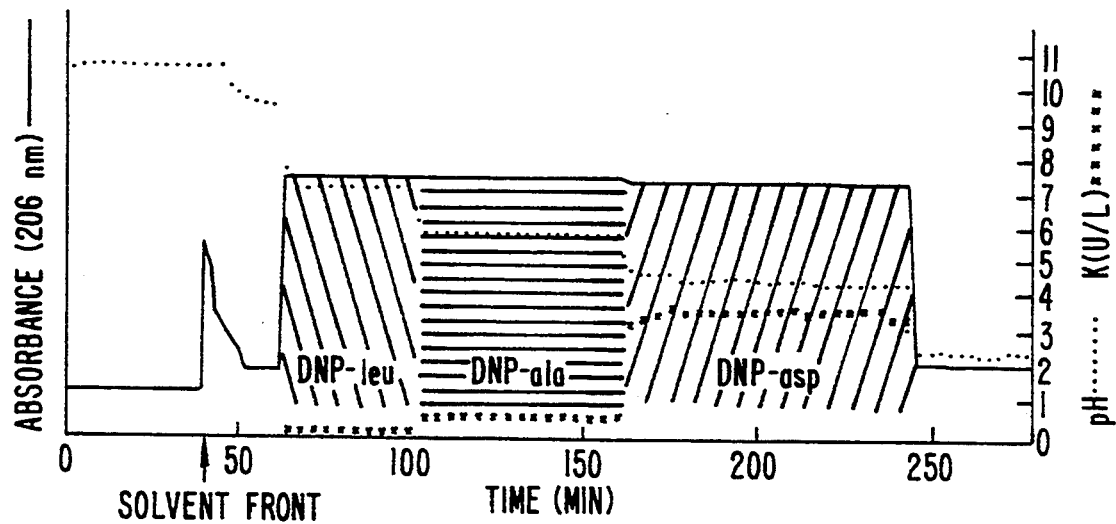
FIG. 5 is a chromatogram obtained from the separation of a mixture containing 1.5 g portions of DNP-leucine, DNP-alanine and DNP-aspartic acid as described in Example 4.

Separation of the mixture of DNP-leu, DNP-ala and DNP-asp was performed using a methyl tertiary-butyl ether/water system by adding $NH_3$ at 0.4% (44 mM) to the aqueous stationary phase and TFA at 0.8% (21.6 mM) to the organic mobile phase. The sample volume was 40 mL consisting of 30 mL acidified aqueous phase and 10 mL methyl tertiary-butyl ether. The sample mixture containing undissolved acids was thoroughly sonicated into a uniform suspension and introduced into the column without filtration. Separation was completed in about 4 hours using a flow rate of 3.3 mL/min and a revolution speed of 600 rpm. The three components were eluted as broad rectangular peaks with sharp boundaries as indicated by the abrupt transition of the partition coefficient (K) and pH levels plotted in FIG. 5.

Example 5

This example illustrates the use of a displacement affinity-ligand separation for non-ionizable samples. The sample to be separated is (±) N-(3,5-dinitrobenzoyl)-t-butyl-leucinamide. The affinity ligand (or chiral selector, cs) is N-dodecanoyl-L-proline-3,5-dimethylanilide and the displacer is N-(3,5-dinitrobenzoyl)-t-butylalaninamide. The chirality of the alaninamide (+ or −) is selected depending on which has the stronger affinity for the chiral selector.

A solvent system of methyl tertiary-butyl ether/water is equilibrated and allowed to settle into its two distinct phases. The chiral selector is added to the upper organic stationary phase to achieve a concentration of from 10 mM to 30 mM. The column is then charged with the stationary phase (containing the cs) followed by the sample (charged through the sample port). The apparatus is rotated while the mobile aqueous phase containing the displacer is eluted through the column. Alternatively, the displacer may be charged to the column following the sample, then eluted with the mobile phase free of a displacer.

The displacer will bind strongly to the chiral selector to displace the two optical isomers which have different association constants with the chiral selector. The displaced isomers then form a succession of rectangular peaks as observed in displacement countercurrent chromatography.

In this particular application of displacement CCC, the mobile phase is an aqueous phase. Additionally, the retainer ligand (cs) is almost permanently retained in the organic stationary phase in the column due to its high hydrophobicity. Moreover, both the sample and ligand are neutral species. For applications in which the sample mixture is more hydrophilic, an aqueous stationary phase and an organic mobile phase can be used.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A method for separating a quantity of an acidic compound from other compounds in a mixture using displacement countercurrent chromatography, comprising:

(a) adding a retainer base to a first liquid phase of two pre-equilibrated immiscible liquid phases and charging a countercurrent chromatographic centrifuge column with said first liquid phase, thereby producing a countercurrent chromatographic centrifuge column charged with said thus basified first liquid phase;

(2) adding a displacer acid to a second liquid phase of said two pre-equilibrated immiscible liquid phases to form an acidic mobile phase;

(3) introducing said mixture into said countercurrent chromatographic centrifuge column thus charged with said basified first liquid phase; and (4) passing said acidic mobile phase through said countercurrent chromatographic centrifuge column thus charged with said mixture and said basified first liquid phase, to elute said acidic compound from said countercurrent chromatographic centrifuge column.

2. The method in accordance with claim 1 wherein said first liquid phase is an aqueous phase.

3. The method in accordance with claim 1 wherein said second liquid phase is an organic phase.

4. The method in accordance with claim 1 wherein said first liquid phase is an aqueous phase and said second liquid phase is an organic phase.

5. The method in accordance with claim 1 wherein said quantity is from 0.01 to 100 grams.

6. The method in accordance with claim 1 wherein said retainer base is a base selected from the group consisting of ammonia, NaOH and KOH.

7. The method in accordance with claim 1 wherein said retainer base is ammonia.

8. The method in accordance with claim 1 wherein said mixture is a suspension.

9. The method in accordance with claim 1 wherein said column is member selected from the group consisting of a helical column and a locular column.

10. A method for separating a quantity of a basic compound from other compounds in a mixture using displacement countercurrent chromatography, comprising:
- (a) adding a retainer acid to a first liquid phase of two pre-equilibrated immiscible liquid phases and charging a countercurrent chromatographic centrifuge column with said first liquid phase, thereby producing a countercurrent chromatographic centrifuge column charged with said thus acidified first liquid phase;
- (2) adding a displacer base to a second liquid phase of said two pre-equilibrated immiscible liquid phases to form a basic mobile phase;
- (3) introducing said mixture into said countercurrent chromatographic centrifuge column thus charged with said acidified first liquid phase; and
- (4) passing said basic mobile phase through said countercurrent chromatographic centrifuge column thus charged with said mixture and said acidified first liquid phase, to elute said basic compound from said countercurrent chromatographic centrifuge column.

11. The method in accordance with claim 10 wherein said first liquid phase is an aqueous phase.

12. The method in accordance with claim 10 wherein said second liquid phase is an organic phase.

13. The method in accordance with claim 10 wherein said first liquid phase is an aqueous phase and said second liquid phase is an organic phase.

14. The method in accordance with claim 10 wherein said quantity is from 0.01 to 100 grams.

15. The method in accordance with claim 10 wherein said mixture is a suspension.

16. The method in accordance with claim 10 wherein said column is a member selected from the group consisting of a helical column and a locular column.

17. A method for separating a quantity of a non-ionizable compound from other compounds in a mixture using displacement countercurrent chromatography, comprising:
- (a) adding an affinity ligand to a first liquid phase of two pre-equilibrated immiscible liquid phases and charging a countercurrent chromatographic centrifuge column with said first liquid phase, thereby producing a countercurrent chromatographic centrifuge column charged with a stationary phase;
- (2) adding a displacer to a second liquid phase of said two pre-equilibrated immiscible liquid phases to form a mobile phase wherein said displacer has a stronger affinity for said affinity ligand than said non-ionizable compound;
- (3) introducing said mixture into said countercurrent chromatographic centrifuge column thus charged with said first liquid phase; and
- (4) passing said mobile phase through said countercurrent chromatographic centrifuge column thus charged with said mixture and said first liquid phase, to elute said non-ionizable compound from said countercurrent chromatographic centrifuge column.

18. The method in accordance with claim 17 wherein said first liquid phase is an aqueous phase and said second liquid phase is an organic phase.

19. The method in accordance with claim 17 wherein said first liquid phase is an organic phase and said second liquid phase is an aqueous phase.

* * * * *